US012790598B2

(12) United States Patent
Kim et al.

(10) Patent No.: US 12,790,598 B2
(45) Date of Patent: Nov. 10, 2026

(54) ACETOHYDROXY ACID SYNTHASE MUTANT AND L-ISOLEUCINE PRODUCTION METHOD USING SAME

(71) Applicant: CJ CHEILJEDANG CORPORATION, Seoul (KR)

(72) Inventors: Heeyeong Kim, Seoul (KR); Kyungrim Kim, Seoul (KR); Woosung Choi, Seoul (KR); Ki Yong Cheong, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 277 days.

(21) Appl. No.: 18/696,968

(22) PCT Filed: Aug. 5, 2022

(86) PCT No.: PCT/KR2022/011610
§ 371 (c)(1),
(2) Date: Mar. 28, 2024

(87) PCT Pub. No.: WO2023/054882
PCT Pub. Date: Apr. 6, 2023

(65) Prior Publication Data

US 2024/0392260 A1 Nov. 28, 2024

(30) Foreign Application Priority Data

Sep. 29, 2021 (KR) ........................ 10-2021-0128912

(51) Int. Cl.
*C12N 9/10* (2006.01)
*C12N 15/77* (2006.01)
*C12P 13/06* (2006.01)

(52) U.S. Cl.
CPC ........... *C12N 9/1022* (2013.01); *C12N 15/77* (2013.01); *C12P 13/06* (2013.01); *C12Y 202/01006* (2013.01)

(58) Field of Classification Search
CPC .................................. C12N 9/10; C12N 15/52
See application file for complete search history.

(56) References Cited

U.S. PATENT DOCUMENTS

| | | | |
|---|---|---|---|
| 6,072,083 A | 6/2000 | Hasegawa et al. | |
| 7,662,943 B2 | 2/2010 | Park et al. | |
| 10,113,190 B2 | 10/2018 | Gerstmeir | |
| 10,273,491 B2 | 4/2019 | Lee et al. | |
| 10,316,297 B2 * | 6/2019 | Jeon | C12N 9/1022 |
| 10,584,338 B2 | 3/2020 | Lee et al. | |
| 2007/0292914 A1 | 12/2007 | Patek et al. | |

FOREIGN PATENT DOCUMENTS

| | | | | |
|---|---|---|---|---|
| CN | 110229797 A | | 9/2019 | |
| CN | 111154748 A | | 5/2020 | |
| KR | 10-1335789 B1 | | 12/2013 | |
| KR | 10-2016-0017389 A | | 2/2016 | |
| KR | 10-1720836 B1 | | 4/2017 | |
| KR | 10-2020-0136813 A | | 10/2019 | |
| KR | 10-1996769 B1 | | 10/2019 | |
| WO | WO-2016021932 A1 | * | 2/2016 | C12Y 202/01006 |

OTHER PUBLICATIONS

International Search Report issued in corresponding International Patent Application No. PCT/KR2022/011610 dated Nov. 11, 2022.
Pearson et al., "Improved tools for biological sequence comparison", Biochemistry, Proc. Natl. Acad. Sci. USA, vol. 85, Apr. 1988, pp. 2444-2448.
Rice et al., "EMBOSS: The European Molecular Biology Open Software Suite", 2000, The European Molecular Biology Open Software Suite, Resource Internet, TIG, vol. 16, No. 6, Jun. 2000, pp. 276-277.
Needleman et al., "A general method applicable to the search for similarities in the amino acid sequence of two proteins", J. Mol. Biol., vol. 48, 1970, pp. 443-453.
Devereux et al., "A comprehensive set of sequence analysis programs for the VAX", Nucleic Acids Research, vol. 12, No. 1, 1984, pp. 387-395.
Altschul et al, "Basic local alignment search tool", J Molec Biol, vol. 215, 1990, pp. 403-410.
Carillo et al., "The Multiple Sequence Alignment Problem in Biology", SIAM Journal on Applied Mathematics, vol. 48, No. 5, 1988, pp. 1073-1082.
Smith et al., "Comparison of biosequences", Advances in Applied Mathematics, vol. 2, Issue 4, 1981, pp. 482-489.
Gribskov et al., "Sigma factors from *E. coli*, B. subtilis, phage SP01, and phage T4 are homologous proteins", Nucleic Acids Res, vol. 14, No. 16, Aug. 26, 1986, pp. 6745-6763.
Guo et al., "Generation of Branched-chain Amino Acids Resistant Corynebacterium glutamicum Acetohydroxy Acid Synthase by Site-directed Mutagenesis", Biotechnology and Bioprocess Engineering, vol. 19, 2014, pp. 456-467.
Extended European Search Report issued in corresponding European Patent Application No. 22876657.2, dated Dec. 17, 2024.

* cited by examiner

*Primary Examiner* — Tekchand Saidha
(74) *Attorney, Agent, or Firm* — Morgan, Lewis & Bockius LLP

(57) ABSTRACT

The present disclosure relates to a novel acetohydroxy acid synthase (AHAS) variant improving L-isoleucine producing ability, a microorganism including the same, and a method of producing L-isoleucine using the microorganism.

13 Claims, No Drawings

Specification includes a Sequence Listing.

SEQUENCE LISTING

```
Sequence total quantity: 24
SEQ ID NO: 1            moltype = AA  length = 172
FEATURE                 Location/Qualifiers
REGION                  1..172
                        note = ilvN
source                  1..172
                        mol_type = protein
                        organism = Corynebacterium sp.
SEQUENCE: 1
MANSDVTRHI LSVLVQDVDG IISRVSGMFT RRAFNLVSLV SAKTETHGIN RITVVVDADE  60
LNIEQITKQL NKLIPVLKVV RLDEETTIAR AIMLVKVSAD STNRPQIVDA ANIFRARVVD  120
VAPDSVVIES TGTPGKLRAL LDVMEPFGIR ELIQSGQIAL NRGPKTMAPA KI          172

SEQ ID NO: 2            moltype = DNA  length = 519
FEATURE                 Location/Qualifiers
misc_feature            1..519
                        note = ilvN
source                  1..519
                        mol_type = genomic DNA
                        organism = Corynebacterium sp.
SEQUENCE: 2
atggctaatt ctgacgtcac ccgccacatc ctgtccgtac tcgttcagga cgtagacgga  60
atcatttccc gcgtatcagg tatgttcacc cgacgcgcat tcaacctcgt gtccctcgtg  120
tctgcaaaga ccgaaacaca cggcatcaac cgcatcacgg ttgttgtcga cgccgacgag  180
ctcaacattg agcagatcac caagcagctc aacaagctga tccccgtgct caaagtcgtg  240
cgacttgatg aagagaccac tatcgcccgc gcaatcatgc tggttaaggt ctctgcggac  300
agcaccaacc gtccgcagat cgtcgacgcc gcgaacatct tccgcgcccg agtcgtcgac  360
gtggctccag actctgtggt tattgaatcc acaggcaccc caggcaagct ccgcgcactg  420
cttgacgtga tggaaccatt cggaatccgc gaactgatcc aatccggaca gattgcactc  480
aaccgcggtc cgaagaccat ggctccggcc aagatctaa                         519

SEQ ID NO: 3            moltype = AA  length = 172
FEATURE                 Location/Qualifiers
REGION                  1..172
                        note = ilvN(A42V)
source                  1..172
                        mol_type = protein
                        organism = synthetic construct
SEQUENCE: 3
MANSDVTRHI LSVLVQDVDG IISRVSGMFT RRAFNLVSLV SVKTETHGIN RITVVVDADE  60
LNIEQITKQL NKLIPVLKVV RLDEETTIAR AIMLVKVSAD STNRPQIVDA ANIFRARVVD  120
VAPDSVVIES TGTPGKLRAL LDVMEPFGIR ELIQSGQIAL NRGPKTMAPA KI          172

SEQ ID NO: 4            moltype = AA  length = 172
FEATURE                 Location/Qualifiers
REGION                  1..172
                        note = ilvN(H47L)
source                  1..172
                        mol_type = protein
                        organism = synthetic construct
SEQUENCE: 4
MANSDVTRHI LSVLVQDVDG IISRVSGMFT RRAFNLVSLV SAKTETLGIN RITVVVDADE  60
LNIEQITKQL NKLIPVLKVV RLDEETTIAR AIMLVKVSAD STNRPQIVDA ANIFRARVVD  120
VAPDSVVIES TGTPGKLRAL LDVMEPFGIR ELIQSGQIAL NRGPKTMAPA KI          172

SEQ ID NO: 5            moltype = AA  length = 172
FEATURE                 Location/Qualifiers
REGION                  1..172
                        note = ilvN(A42V, H47L)
source                  1..172
                        mol_type = protein
                        organism = synthetic construct
SEQUENCE: 5
```

```
MANSDVTRHI LSVLVQDVDG IISRVSGMFT RRAFNLVSLV SVKTETLGIN RITVVVDADE  60
LNIEQITKQL NKLIPVLKVV RLDEETTIAR AIMLVKVSAD STNRPQIVDA ANIFRARVVD  120
VAPDSVVIES TGTPGKLRAL LDVMEPFGIR ELIQSGQIAL NRGPKTMAPA KI          172

SEQ ID NO: 6           moltype = DNA  length = 35
FEATURE                Location/Qualifiers
misc_feature           1..35
                       note = primer 1
source                 1..35
                       mol_type = other DNA
                       organism = synthetic construct
SEQUENCE: 6
tcgagctcgg taccccgctt ttgcactcat cgagc                             35

SEQ ID NO: 7           moltype = DNA  length = 23
FEATURE                Location/Qualifiers
misc_feature           1..23
                       note = primer 2
source                 1..23
                       mol_type = other DNA
                       organism = synthetic construct
SEQUENCE: 7
cacgatcaga tgtgcatcat cat                                          23

SEQ ID NO: 8           moltype = DNA  length = 23
FEATURE                Location/Qualifiers
misc_feature           1..23
                       note = primer 3
source                 1..23
                       mol_type = other DNA
                       organism = synthetic construct
SEQUENCE: 8
atgatgatgc acatctgatc gtg                                          23

SEQ ID NO: 9           moltype = DNA  length = 35
FEATURE                Location/Qualifiers
misc_feature           1..35
                       note = primer 4
source                 1..35
                       mol_type = other DNA
                       organism = synthetic construct
SEQUENCE: 9
ctctagagga tccccgagca tcttccaaaa ccttg                             35

SEQ ID NO: 10          moltype = DNA  length = 35
FEATURE                Location/Qualifiers
misc_feature           1..35
                       note = primer 5
source                 1..35
                       mol_type = other DNA
                       organism = synthetic construct
SEQUENCE: 10
tcgagctcgg tacccatgag tgaaacatac gtgtc                             35

SEQ ID NO: 11          moltype = DNA  length = 39
FEATURE                Location/Qualifiers
misc_feature           1..39
                       note = primer 6
source                 1..39
                       mol_type = other DNA
                       organism = synthetic construct
SEQUENCE: 11
gcgcttgagg tactctgcca gcgcgatgtc atcatccgg                         39

SEQ ID NO: 12          moltype = DNA  length = 39
FEATURE                Location/Qualifiers
misc_feature           1..39
                       note = primer 7
source                 1..39
                       mol_type = other DNA
                       organism = synthetic construct
SEQUENCE: 12
ccggatgatg acatcgcgct ggcagagtac ctcaagcgc                         39

SEQ ID NO: 13          moltype = DNA  length = 34
FEATURE                Location/Qualifiers
misc_feature           1..34
                       note = primer 8
source                 1..34
```

```
                        mol_type = other DNA
                        organism = synthetic construct
SEQUENCE: 13
ctctagagga tcccccgtca ccgacacctc caca                             34

SEQ ID NO: 14           moltype = DNA  length = 30
FEATURE                 Location/Qualifiers
misc_feature            1..30
                        note = primer 9
source                  1..30
                        mol_type = other DNA
                        organism = synthetic construct
SEQUENCE: 14
cgagctcggt acccatggct aattctgacg                                  30

SEQ ID NO: 15           moltype = DNA  length = 30
FEATURE                 Location/Qualifiers
misc_feature            1..30
                        note = primer 10
source                  1..30
                        mol_type = other DNA
                        organism = synthetic construct
SEQUENCE: 15
tagaggatcc ccttagatct tggccggagc                                  30

SEQ ID NO: 16           moltype = DNA  length = 1338
FEATURE                 Location/Qualifiers
misc_feature            1..1338
                        note = hom(R407H)
source                  1..1338
                        mol_type = other DNA
                        organism = synthetic construct
SEQUENCE: 16
atgacctcag catctgcccc aagctttaac cccggcaagg gtcccggctc agcagtcgga  60
attgcccttt taggattcgg aacagtcggc actgaggtga tgcgtctgat gaccgagtac  120
ggtgatgaac ttgcgcaccg cattggtggc ccactggagg ttcgtggcat tgctgtttct  180
gatatctcaa agccacgtga aggcgttgca cctgagctgc tcactgagga cgcttttgca  240
ctcatcgagc gcgaggatgt tgacatcgtc gttgaggtta tcggcggcat tgagtaccca  300
cgtgaggtag ttctcgcagc tctgaaggcc ggcaagtctg ttgttaccgc caataaggct  360
cttgttgcag ctcactctgc tgagcttgct gatgcagcgg aagccgcaaa cgttgacctg  420
tacttcgagg ctgctgttgc aggcgcaatt ccagtggttg gcccactgcg tcgctccctg  480
gctggcgatc agatccagtc tgtgatgggc atcgttaacg gcaccaccaa cttcatcttg  540
gacgccatgg attccaccgg cgctgactat gcagattctt ggctgaggc aactcgtttg  600
ggttacgccg aagctgatcc aactgcagac gtcgaaggcc atgacgccgc atccaaggct  660
gcaattttgg catccatcgc tttccacacc cgtgttaccg cggatgatgt gtactgcgaa  720
ggtatcagca acatcagcgc tgccgacatt gaggcagcac agcaggcagg ccacaccatc  780
aagttgttgg ccatctgtga gaagttcacc aacaaggaag gaaagtcggc tatttctgct  840
cgcgtgcacc cgactctatt acctgtgtcc cacccactgg cgtcggtaaa caagtccttt  900
aatgcaatct ttgttgaagc agaagcagct ggtcgcctga tgttctacgg aaacggtgca  960
ggtggcgcgc caaccgcgtc tgctgtgctt ggcgacgtcg ttggtgccgc acgaaacaag  1020
gtgcacggtg gccgtgctcc aggtgagtcc acctacgcta acctgccgat cgctgatttc  1080
ggtgagacca ccactcgtta ccacctcgac atggatgtgg aagatcgcgt gggggtttg  1140
gctgaattgg ctagcctgtt ctctgagcaa ggaatctccc tgcgtacaat ccgacaggaa  1200
gagcgcgatg atgatgcaca tctgatcgtg gtcacccact ctgcgctgga atctgatctt  1260
tcccgcaccg ttgaactgct gaaggctaag cctgttgtta aggcaatcaa cagtgtgatc  1320
cgcctcgaaa gggactaa                                               1338

SEQ ID NO: 17           moltype = DNA  length = 1311
FEATURE                 Location/Qualifiers
misc_feature            1..1311
                        note = ilvA(T381A, F383A)
source                  1..1311
                        mol_type = other DNA
                        organism = synthetic construct
SEQUENCE: 17
atgagtgaaa catacgtgtc tgagaaaagt ccaggagtga tggctagcgg agcggagctg  60
attcgtgccg ccgacattca aacggcgcag gcacgaattt cctccgtcat tgcaccaact  120
ccattgcagt attgccctcg tctttctgag gaaaccggag cggaaatcta ccttaagcgt  180
gaggatctgc aggatgttcg ttcctacaag atccgcggtg cgctgaactc tggagcgcag  240
ctcactcagg agcagcgcga tgcaggtatc gttgccgcat ctgcaggtaa ccatgcccag  300
ggcgtggcct atgtgtgcaa gtccttgggc gttcagggac gcatctatgt tcctgtgcag  360
actccaaagc aaaagcgtga ccgcatcatg gttcacggcg gagagtttgt ctccttggtg  420
gtcactggca ataacttcga cgaagcatcg gctgcagcgc atgaagatgc agagcgcacc  480
ggcgcaacgc tgatcgagcc tttcgatgct cgcaacaccg tcatcggtca gggtacagtg  540
gctgctgaga tcttgtcgca gctgacttcc atgggcaaga gtgcagatca cgtgatggtt  600
ccagtcggcg gtggcggact tcttgcaggt gtggtcagct acatggctga tatggcacct  660
cgcactgcga tcgttggtat cgaaccagcg ggagcagcat ccatgcaggc tgcattgcac  720
aatggtggac caatcacttt ggagactgtt gatccctttg tggacggcgc agcagtcaaa  780
cgtgtcggag atctcaacta caccatcgtg gagaagaacc agggtcgcgt gcacatgatg  840
```

-continued

```
agcgcgaccg agggcgctgt gtgtactgag atgctcgatc tttaccaaaa cgaaggcatc  900
atcgcggagc ctgctggcgc gctgtctatc gctgggttga aggaaatgtc ctttgcacct  960
ggttctgtcg tggtgtgcat catctctggt ggcaacaacg atgtgctgcg ttatgcggaa  1020
atcgctgagc gctccttggt gcaccgcggt ttgaagcact acttcttggt gaacttcccg  1080
caaaagcctg gtcagttgcg tcacttcctg gaagatatcc tgggaccgga tgatgacatc  1140
gcgctggcag agtacctcaa gcgcaacaac cgtgagaccg gtactgcgtt ggtgggtatt  1200
cacttgagtg aagcatcagg attggattct ttgctggaac gtatggagga atcggcaatt  1260
gattcccgtc gcctcgagcc gggcacccct gagtacgaat acttgaccta a           1311

SEQ ID NO: 18          moltype = DNA  length = 30
FEATURE                Location/Qualifiers
misc_feature           1..30
                       note = primer 11
source                 1..30
                       mol_type = other DNA
                       organism = synthetic construct
SEQUENCE: 18
ttcggtctta acagacacga gggacacgag                                   30

SEQ ID NO: 19          moltype = DNA  length = 30
FEATURE                Location/Qualifiers
misc_feature           1..30
                       note = primer 12
source                 1..30
                       mol_type = other DNA
                       organism = synthetic construct
SEQUENCE: 19
gtgtccctcg tgtctgttaa gaccgaaaca                                   30

SEQ ID NO: 20          moltype = DNA  length = 30
FEATURE                Location/Qualifiers
misc_feature           1..30
                       note = primer 13
source                 1..30
                       mol_type = other DNA
                       organism = synthetic construct
SEQUENCE: 20
cggttgatgc cgagtgtttc ggtctttgca                                   30

SEQ ID NO: 21          moltype = DNA  length = 30
FEATURE                Location/Qualifiers
misc_feature           1..30
                       note = primer 14
source                 1..30
                       mol_type = other DNA
                       organism = synthetic construct
SEQUENCE: 21
aagaccgaaa cactcggcat caaccgcatc                                   30

SEQ ID NO: 22          moltype = DNA  length = 519
FEATURE                Location/Qualifiers
misc_feature           1..519
                       note = ilvN(A42V)
source                 1..519
                       mol_type = other DNA
                       organism = synthetic construct
SEQUENCE: 22
atggctaatt ctgacgtcac ccgccacatc ctgtccgtac tcgttcagga cgtagacgga  60
atcatttccc gcgtatcagg tatgttcacc cgacgcgcat tcaacctcgt gtccctcgtg  120
tctgttaaga ccgaaacaca cggcatcaac cgcatcacgg ttgttgtcga cgccgacgag  180
ctcaacattg agcagatcac caagcagctc aacaagctga tccccgtgct caaagtcgtg  240
cgacttgatg aagagaccac tatcgcccgc gcaatcatgc tggttaaggt ctctgcggac  300
agcaccaacc gtccgcagat cgtcgacgcc gcgaacatct tccgcgcccg agtcgtcgac  360
gtggctccag actctgtggt tattgaatcc acaggcaccc caggcaagct ccgcgcactg  420
cttgacgtga tggaaccatt cggaatccgc gaactgatcc aatccggaca gattgcactc  480
aaccgcggtc cgaagaccat ggctccggcc aagatctaa                         519

SEQ ID NO: 23          moltype = DNA  length = 519
FEATURE                Location/Qualifiers
misc_feature           1..519
                       note = ilvN(H47L)
source                 1..519
                       mol_type = other DNA
                       organism = synthetic construct
SEQUENCE: 23
atggctaatt ctgacgtcac ccgccacatc ctgtccgtac tcgttcagga cgtagacgga  60
atcatttccc gcgtatcagg tatgttcacc cgacgcgcat tcaacctcgt gtccctcgtg  120
tctgcaaaga ccgaaacact cggcatcaac cgcatcacgg ttgttgtcga cgccgacgag  180
ctcaacattg agcagatcac caagcagctc aacaagctga tccccgtgct caaagtcgtg  240
```

-continued

```
cgacttgatg aagagaccac tatcgcccgc gcaatcatgc tggttaaggt ctctgcggac  300
agcaccaacc gtccgcagat cgtcgacgcc gcgaacatct tccgcgcccg agtcgtcgac  360
gtggctccag actctgtggt tattgaatcc acaggcaccc caggcaagct ccgcgcactg  420
cttgacgtga tggaaccatt cggaatccgc gaactgatcc aatccggaca gattgcactc  480
aaccgcggtc cgaagaccat ggctccggcc aagatctaa                         519

SEQ ID NO: 24          moltype = DNA  length = 519
FEATURE                Location/Qualifiers
misc_feature           1..519
                       note = ilvN(A42V, H47L)
source                 1..519
                       mol_type = other DNA
                       organism = synthetic construct
SEQUENCE: 24
atggctaatt ctgacgtcac ccgccacatc ctgtccgtac tcgttcagga cgtagacgga  60
atcatttccc gcgtatcagg tatgttcacc cgacgcgcat tcaacctcgt gtccctcgtg  120
tctgttaaga ccgaaacact cggcatcaac cgcatcacgg ttgttgtcga cgccgacgag  180
ctcaacattg agcagatcac caagcagctc aacaagctga tccccgtgct caaagtcgtg  240
cgacttgatg aagagaccac tatcgcccgc gcaatcatgc tggttaaggt ctctgcggac  300
agcaccaacc gtccgcagat cgtcgacgcc gcgaacatct tccgcgcccg agtcgtcgac  360
gtggctccag actctgtggt tattgaatcc acaggcaccc caggcaagct ccgcgcactg  420
cttgacgtga tggaaccatt cggaatccgc gaactgatcc aatccggaca gattgcactc  480
aaccgcggtc cgaagaccat ggctccggcc aagatctaa                         519
```

ACETOHYDROXY ACID SYNTHASE MUTANT AND L-ISOLEUCINE PRODUCTION METHOD USING SAME

A computer readable xml file, entitled "133660-04-9040-US_Sequence_Listing_ST26.xml," created on or about Mar. 28, 2024, with a file size of 36,549 bytes contains the sequence listing for this application and is hereby incorporated by reference in its entirety.

TECHNICAL FIELD

The present disclosure relates to a novel acetohydroxy acid synthase (AHAS) variant improving L-isoleucine producing ability, a microorganism including the same, and a method of producing L-isoleucine using the microorganism.

BACKGROUND ART

L-Isoleucine is one of the branched-chain amino acids among a total of 20 amino acids, and is classified as an essential amino acid and used in the animal feed, food additive, and pharmaceutical fields. Since L-isoleucine has functions such as energy generation after metabolism, hemoglobin production, blood sugar control, muscle generation and repair, etc., its use is increasing in the fields of animal feeds as well as infusion solutions, nutrition supplements, and sports nutrition supplements.

Based on this trend, various microorganisms and variants thereof are used for L-amino acid production (U.S. Pat. No. 10,113,190), and even in this case, many by-products other than L-isoleucine are produced, which are substances that greatly affect the purity of L-isoleucine in the purification step, and therefore, a method capable of removing the by-products is required. In this regard, methods of purifying L-isoleucine which have been developed to increase the purity of L-isoleucine have a disadvantage of requiring an additional separate purification process (U.S. Pat. No. 6,072,083), and thus it is necessary to develop a method of increasing the purity of L-isoleucine.

DISCLOSURE

Technical Problem

With regard to acetohydroxy acid synthase (AHAS), which is one of the proteins in the L-isoleucine production pathway, the present inventors have investigated a variant thereof, and they found that L-isoleucine producing ability of a strain may be improved by the variant, thereby completing the present disclosure.

Technical Solution

An object of the present disclosure is to provide an acetohydroxy acid synthase (AHAS) variant, in which an amino acid corresponding to position 42 and an amino acid corresponding to position 47 in an amino acid sequence of SEQ ID NO: 1 are each substituted with another amino acid.

Another object of the present disclosure is to provide a polynucleotide encoding the variant of the present disclosure.

Still another object of the present disclosure is to provide a strain of the genus *Corynebacterium* including the variant of the present disclosure; or the polynucleotide encoding the variant.

Still another object of the present disclosure is to provide a method of producing L-isoleucine, the method including the step of culturing, in a medium, the strain of the genus *Corynebacterium* including the variant of the present disclosure; or the polynucleotide encoding the variant.

Advantageous Effects

A microorganism expressing an acetohydroxy acid synthase variant of the present disclosure may remarkably improve the L-isoleucine production, as compared to a strain not expressing the same, and thus L-isoleucine may be effectively produced using the same. Accordingly, a wide range of industrial applications thereof, such as in foods, feeds, medicines, etc., in which L-isoleucine is used, may be expected.

DETAILED DESCRIPTION OF PREFERRED EMBODIMENTS

The present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below. Further, a number of papers and patent documents are referenced and cited throughout this specification. The disclosures of the cited papers and patent documents are incorporated herein by reference in their entirety to further clarify the level and scope of the subject matter to which the present disclosure pertains.

An aspect of the present disclosure provides an acetohydroxy acid synthase (AHAS) variant, in which an amino acid corresponding to position 42 and an amino acid corresponding to position 47 in an amino acid sequence of SEQ ID NO: 1 are each substituted with another amino acid.

In one embodiment, the amino acid corresponding to position 42 may be substituted with valine.

In another embodiment, the amino acid corresponding to position 47 may be substituted with leucine.

The variant of the present disclosure may include an amino acid sequence having alanine which is substituted for the amino acid corresponding to position 42 and leucine, which is substituted for the amino acid corresponding to position 47, based on the amino acid sequence represented by SEQ ID NO: 1, which is a parent sequence, and having at least 70% or more, 75% or more, 80% or more, 85% or more, 90% or more, 95% or more, 96% or more, 97% or more, 98% or more, 99% or more, 99.5% or more, or 99.7% or more, and less than 100% homology or identity to the amino acid sequence represented by SEQ ID NO: 1. It is also apparent that a variant having an amino acid sequence having deletion, modification, substitution, conservative substitution, or addition of some amino acids also falls within the scope of the present disclosure as long as the amino acid sequence has such a homology or identity and exhibits efficacy corresponding to that of the variant of the present disclosure.

Examples thereof include those having sequence addition or deletion that does not alter the function of the variant of the present disclosure at the N-terminus or C-terminus of the amino acid sequence, and/or inside the amino acid sequence, naturally occurring mutation, silent mutation, or conservative substitution.

The "conservative substitution" means substitution of one amino acid with another amino acid having similar structural and/or chemical properties. Such an amino acid substitution may generally occur based on similarity in the polarity, charge, solubility, hydrophobicity, hydrophilicity, and/or amphipathic nature of the residues. Usually, conservative substitution may hardly affect or not affect the activity of the proteins or polypeptides.

As used herein, the term "variant" refers to a polypeptide which has an amino acid sequence different from that of the variant before being varied by conservative substitution and/or modification of one or more amino acids but maintains the functions or properties. Such a variant may be generally identified by modifying one or more amino acids of the amino acid sequence of the polypeptide and evaluating the properties of the modified polypeptide. In other words, ability of the variant may be increased, unchanged, or decreased, as compared to that of the polypeptide before being varied. Some variants may include variants in which one or more portions such as an N-terminal leader sequence or a transmembrane domain have been removed. Other variants may include variants in which a portion of the N- and/or C-terminus has been removed from the mature protein. The term "variant" may be used interchangeably with terms such as modification, modified polypeptide, modified protein, mutant, mutein, and divergent, and is not limited thereto as long as it is a term used with the meaning of variation.

The variant may include deletions or additions of amino acids that have minimal effect on the properties and secondary structure of the polypeptide. For example, a signal (or leader) sequence that is co-translationally or post-translationally involved in the protein translocation may be conjugated to the N-terminus of the variant. The variant may be conjugated with other sequences or linkers so as to be identified, purified, or synthesized.

As used herein, the "parent sequence" refers to a reference sequence that becomes a modified polypeptide by introducing a modification. In other words, the parent sequence is a starting sequence and may be a target for introducing variation such as substitution, insertion, and/or deletion, etc. The parent sequence may be a naturally occurring or wild-type sequence, or a variant in which one or more substitutions, insertions, or deletions have occurred in the naturally occurring or wild-type sequence, or may be an artificially synthesized sequence.

As used herein, the term "homology" or "identity" means the degree of similarity between two given amino acid sequences or base sequences, and may be expressed as a percentage. The terms "homology" and "identity" may often be used interchangeably.

The sequence homology or identity of a conserved polynucleotide or polypeptide is determined by standard alignment algorithms, and the default gap penalty established by a program used may be used together. Substantially, homologous or identical sequences are generally capable of being hybridized with the entirety or at least about 50% or more, 60% or more, 70% or more, 80% or more, or 90% more of the entirety of the sequence under moderately or highly stringent conditions. It is apparent that hybridization also includes hybridization with a polynucleotide including a general codon or a codon in consideration of codon degeneracy.

Whether or not any two polynucleotide or polypeptide sequences have homology, similarity, or identity may be determined using known computer algorithms such as the "FASTA" program, for example, using default parameters as in Pearson et al. (1988) *Proc. Natl. Acad. Sci. USA* 85:2444. Alternatively, the homology, similarity, or identity may be determined using Needleman-Wunsch algorithm (Needleman and Wunsch, 1970, *J. Mol. Biol.* 48:443-453) as performed in the Needleman program of the EMBOSS package (EMBOSS: The European Molecular Biology Open Software Suite, Rice et al., 2000. *Trends Genet.* 16:276-277) (version 5.0.0 or later) (including GCG program package (Devereux, J., et al., *Nucleic Acids Research* 12:387 (1984)), BLASTP, BLASTN, FASTA (Atschul, S. F., et al., *J MOLEC BIOL* 215:403 (1990); *Guide to Huge Computers*, Martin J. Bishop, ed., Academic Press, San Diego, 1994, and CARILLO et al. (1988) *SIAM J Applied Math* 48:1073). For example, BLAST of the National Center for Biotechnology Information or ClustalW may be used to determine the homology, similarity, or identity.

The homology, similarity, or identity of polynucleotides or polypeptides may be determined by comparing sequence information using, for example, a GAP computer program such as Needleman et al. (1970), *J Mol Biol.* 48:443 as announced in, for example, Smith and Waterman, *Adv. Appl. Math* (1981) 2:482. In summary, the GAP program may be defined as the value acquired by dividing the number of similarly aligned symbols (i.e., nucleotides or amino acids) by the total number of symbols in the shorter of two sequences. The default parameters for the GAP program may include (1) a binary comparison matrix (including values of 1 for identity and 0 for non-identity) and a weighted comparison matrix of Gribskov et al. (1986) *Nucl. Acids Res.* 14:6745 (or EDNAFULL (EMBOSS version of NCBI NUC4.4) substitution matrix) as disclosed in Schwartz and Dayhoff, eds., *Atlas Of Protein Sequence And Structure*, National Biomedical Research Foundation, pp. 353-358 (1979); (2) a penalty of 3.0 for each gap and an additional 0.10 penalty for each symbol in each gap (or gap opening penalty of 10, gap extension penalty of 0.5); and (3) no penalty for end gaps.

The variant of the present disclosure may have acetohydroxy acid synthase (AHAS) activity. Further, the variant of the present disclosure may have activity to increase the L-isoleucine producing ability, as compared to a wild-type polypeptide having the acetohydroxy acid synthase activity.

As used herein, the "acetohydroxy acid synthase (AHAS)" is the first enzyme in the L-valine biosynthesis, and is also called acetolactate synthase. Acetohydroxy acid synthase catalyzes decarboxylation of pyruvate and its condensation reaction with other pyruvic acid molecules to produce acetolactate, which is a precursor of valine, or catalyzes decarboxylation of pyruvate and its condensation reaction with 2-ketobutyrate to produce acetohydroxybutyrate, which is a precursor of isoleucine.

The acetohydroxy acid synthase is encoded by two genes, ilvB and ilvN. The ilvB gene encodes a large subunit of acetohydroxy acid synthase and the ilvN gene encodes a small subunit of acetohydroxy acid synthase. Of them, the small subunit encoded by the ilvN gene is considered to be critically involved in feedback inhibition. The "feedback inhibition" means that an end product of an enzyme system inhibits a reaction at an early stage of the enzyme system. With respect to the objects of the present disclosure, the acetohydroxy acid synthase may be acetohydroxy acid synthase encoded by the ilvN gene.

A sequence of the acetohydroxy acid synthase encoded by the ilvN gene may be obtained from NCBI's GenBank, which is a known database, and specifically, may have the amino acid sequence of SEQ ID NO: 1, but is not limited thereto.

As used herein, the term "corresponding to" refers to amino acid residues at positions listed in the polypeptide or amino acid residues that are similar, identical, or homologous to those listed in the polypeptide. Identifying the amino acid at the corresponding position may be determining a specific amino acid in a sequence that refers to a specific sequence. As used herein, the "corresponding region" generally refers to a similar or corresponding position in a related protein or a reference protein.

For example, an arbitrary amino acid sequence is aligned with SEQ ID NO: 1, and based on this, each amino acid residue of the amino acid sequence may be numbered with reference to the numerical position of the amino acid residue corresponding to the amino acid residue of SEQ ID NO: 1. For example, a sequence alignment algorithm as described in the present disclosure may determine the position of an amino acid or a position at which modification such as substitution, insertion, or deletion occurs through comparison with that in a query sequence (also referred to as a "reference sequence").

For such alignments, for example, the Needleman-Wunsch algorithm (Needleman and Wunsch, 1970, *J Mol Biol.* 48:443-453), the Needleman program of the EMBOSS package (EMBOSS: The European Molecular Biology Open Software Suite, Rice et al., 2000), *Trends Genet.* 16:276-277), etc. may be used, but are not limited thereto, and a sequence alignment program, a pairwise sequence comparison algorithm, etc. which is known in the art may be appropriately used.

Specifically, the variant of the present disclosure may have, include, or consist of an amino acid sequence represented by SEQ ID NO: 5, or may essentially consist of the amino acid sequence.

Another aspect of the present disclosure provides a polynucleotide encoding the variant of the present disclosure.

As used herein, the term "polynucleotide" is a DNA or RNA strand having a certain length or more as a polymer of nucleotides in which nucleotide monomers are connected in a long chain by covalent bonds, and more specifically, means a polynucleotide fragment encoding the variant.

The polynucleotide encoding the variant of the present disclosure may include a nucleotide sequence encoding the amino acid sequence represented by SEQ ID NO: 3 or SEQ ID NO: 4 or SEQ ID NO: 5. As an example of the present disclosure, the polynucleotide of the present disclosure may have or include a sequence of SEQ ID NO: 24. Further, the polynucleotide of the present disclosure may consist of or essentially consist of the sequence of SEQ ID NO: 24.

In the polynucleotide of the present disclosure, various modifications may be made in the coding region as long as the amino acid sequence of the variant of the present disclosure is not changed in consideration of codon degeneracy or codons preferred in organisms that are intended to express the variant of the present disclosure. Specifically, the polynucleotide of the present disclosure may have or include a base sequence having 70% or more, 75% or more, 80% or more, 85% or more, 90% or more, 95% or more, 96% or more, 97% or more, or 98% or more, and less than 100% homology or identity to the sequence of SEQ ID NO: 2 or may consist of or essentially consist of a base sequence having 70% or more, 75% or more, 80% or more, 85% or more, 90% or more, 95% or more, 96% or more, 97% or more, or 98% or more, and less than 100% homology or identity to the sequence of SEQ ID NO: 2, but is not limited thereto. Here, in the sequence having homology or identity, the codon encoding the amino acid corresponding to position 42 of SEQ ID NO: 1 may be one of the codons encoding valine, and the codon encoding the amino acid corresponding to position 47 of SEQ ID NO: 1 may be one of the codons encoding leucine.

Further, the polynucleotide of the present disclosure may include a probe that may be prepared from a known gene sequence, for example, a sequence without limitation as long as it is a sequence that is able to hybridize with a complementary sequence to the entirety or a part of the polynucleotide sequence of the present disclosure under stringent conditions. The "stringent conditions" mean conditions that enable specific hybridization between polynucleotides. These conditions are specifically described in documents (see J. Sambrook et al., *Molecular Cloning, A Laboratory Manual,* 2nd Edition, Cold Spring Harbor Laboratory press, Cold Spring Harbor, New York, 1989; F. M. Ausubel et al., *Current Protocols in Molecular Biology*, John Wiley & Sons, Inc., New York, 9.50-9.51, 11.7-11.8). Examples thereof include a condition in which polynucleotides having higher homology or identity, i.e., polynucleotides having 70% or more, 75% or more, 80% or more, 85% or more, 90% or more, 95% or more, 96% or more, 97% or more, 98% or more, or 99% or more homology or identity are hybridized with each other while polynucleotides having lower homology or identity are not hybridized with each other, or a condition in which washing is performed once, specifically, twice to three times at a salt concentration and temperature equivalent to 60° C., 1×SSC, 0.1% SDS, specifically 60° C., 0.1×SSC, 0.1% SDS, more specifically 68° C., 0.1×SSC, 0.1% SDS, which are washing conditions for common Southern hybridization.

Hybridization requires that two nucleic acids have complementary sequences, although mismatches between bases are allowed depending on the stringency of hybridization. The term "complementary" is used to describe the relation between nucleotide bases capable of being hybridized with each other. For example, with regard to DNA, adenine is complementary to thymine and cytosine is complementary to guanine. Hence, the polynucleotide of the present disclosure may also include substantially similar nucleic acid sequences as well as isolated nucleic acid fragments that are complementary to the entire sequence.

Specifically, a polynucleotide having homology or identity to the polynucleotide of the present disclosure may be detected using a hybridization condition including a hybridization step at a $T_m$ value of 55° C. and the above-described conditions. Further, the $T_m$ value may be 60° C., 63° C., or 65° C., but is not limited thereto, and may be appropriately adjusted by those skilled in the art according to the purpose.

The appropriate stringency to hybridize the polynucleotide depends on the length and degree of complementarity of the polynucleotide, and the variables are well known in the art (e.g., J. Sambrook et al., supra).

Still another aspect of the present disclosure provides a vector including the polynucleotide of the present disclosure. The vector may be an expression vector for expressing the polynucleotide in a host cell, but is not limited thereto.

The vector of the present disclosure may include a DNA construct including a polynucleotide sequence encoding a polypeptide of interest which is operably linked to a suitable expression regulatory region (or expression control sequence) so that the polypeptide of interest may be expressed in a suitable host. The expression regulatory region may include a promoter capable of initiating transcription, any operator sequence for controlling the transcription, a sequence encoding a suitable mRNA ribosome binding site, and a sequence controlling termination of transcription and translation. The vector may be transformed into a suitable host cell and then replicated or function independently of the host genome, or may be integrated into the genome itself.

The vector used in the present disclosure is not particularly limited, but any vector known in the art may be used. Examples of commonly used vectors include natural or recombinant plasmids, cosmids, viruses, and bacteriophages. For example, pWE15, M13, MBL3, MBL4, IXII, ASHII, APII, t10, t11, Charon4A, Charon21A, etc. may be used as a phage vector or a cosmid vector, and pDZ system, pBR system, pUC system, pBluescript II system, pGEM system, pTZ system, pCL system, pET system, etc. may be used as a plasmid vector. Specifically, pDZ, pDC, pDCM2, pACYC177, pACYC184, pCL, pECCG117, pUC19, pBR322, pMW118, pCC1BAC vector, etc. may be used.

For example, a polynucleotide encoding a polypeptide of interest may be inserted into a chromosome through a vector for intracellular chromosome insertion. Insertion of the polynucleotide into the chromosome may be performed by any method known in the art, for example, homologous recombination, but is not limited thereto. The vector may further include a selection marker for the confirmation of chromosome insertion. The selection marker is for selecting the cells transformed with vectors, i.e., for confirming the insertion of a nucleic acid molecule of interest, and markers that confer selectable phenotypes such as drug resistance, auxotrophy, resistance to cytotoxic agents, or expression of surface polypeptides may be used. In an environment treated with a selective agent, only cells expressing the selection marker survive or exhibit other phenotypic traits, and thus transformed cells may be selected.

As used herein, the term "transformation" means that a vector including a polynucleotide encoding a target polypeptide is introduced into a host cell or a microorganism so that the polypeptide encoded by the polynucleotide may be expressed in the host cell. The transformed polynucleotide may be located regardless of the position, either by being inserted into the chromosome of the host cell or located outside the chromosome as long as it may be expressed in the host cell. The polynucleotide includes DNA and/or RNA encoding a polypeptide of interest. The polynucleotide may be introduced in any form as long as it may be introduced into a host cell and expressed. For example, the polynucleotide may be introduced into a host cell in the form of an expression cassette, which is a gene construct containing all elements required for self-expression. The expression cassette may usually include a promoter operably linked to the polynucleotide, a transcription termination signal, a ribosome binding site, and a translation termination signal. The expression cassette may be in the form of an expression vector capable of self-replicating. The polynucleotide may be introduced into a host cell in its own form and operably linked to a sequence required for expression in the host cell, but is not limited thereto.

Further, the term "operably linked" means that the polynucleotide sequence is functionally linked to a promoter sequence that initiates and mediates transcription of the polynucleotide encoding the variant of interest of the present disclosure.

Still another aspect of the present disclosure provides a strain of the genus *Corynebacterium* including the variant of the present disclosure or the polynucleotide of the present disclosure.

The strain of the present disclosure may include the modified polypeptide of the present disclosure, the polynucleotide encoding the polypeptide, or the vector including the polynucleotide of the present disclosure.

As used herein, the term "strain (or microorganism)" includes all of wild-type microorganisms or naturally or artificially genetically modified microorganisms, and it may be a microorganism in which a specific mechanism is weakened or strengthened due to insertion of a foreign gene or an activity enhancement or inactivation of an endogenous gene, and it may be a microorganism including genetic modification for production of a polypeptide, protein, or product of interest.

The strain of the present disclosure may be a strain including any one or more of the variant of the present disclosure, the polynucleotide of the present disclosure, and a vector including the polynucleotide of the present disclosure; a strain modified to express the variant of the present disclosure or the polynucleotide of the present disclosure; a strain (e.g., a recombinant strain) expressing the variant of the present disclosure or the polynucleotide of the present disclosure; or a strain (e.g., a recombinant strain) having the activity of the variant of the present disclosure, but is not limited thereto.

The strain of the present disclosure may be a strain having L-isoleucine producing ability.

The strain of the present disclosure may be a microorganism naturally having acetohydroxy acid synthase or L-isoleucine producing ability, or a microorganism in which the variant of the present disclosure or the polynucleotide encoding the variant (or a vector including the polynucleotide) is introduced into a parent strain that does not have acetohydroxy acid synthase or L-isoleucine producing ability and/or in which L-isoleucine producing ability is conferred on the parent strain, but is not limited thereto.

For example, the strain of the present disclosure is a cell or microorganism that is transformed with the polynucleotide of the present disclosure or a vector including the polynucleotide encoding the variant of the present disclosure to express the variant of the present disclosure. With respect to the objects of the present disclosure, the strain of the present disclosure may include all microorganisms that include the variant of the present disclosure and is able to produce L-isoleucine. For example, the strain of the present disclosure may be a recombinant strain in which the polynucleotide encoding the variant of the present disclosure is introduced into a natural wild-type microorganism or a microorganism producing L-isoleucine to express the acetohydroxy acid synthase variant and to have an increased L-isoleucine producing ability. The recombinant strain having the increased L-isoleucine producing ability may be a microorganism having an increased L-isoleucine producing ability, as compared to a natural wild-type microorganism or acetohydroxy acid synthase unmodified microorganism (i.e., a microorganism expressing the wild-type acetohydroxy acid synthase (SEQ ID NO: 1) or a microorganism that does not express the modified protein (SEQ ID NO: 5), but is not limited thereto. For example, the acetohydroxy acid synthase unmodified microorganism, which is a target strain to compare whether or not the L-isoleucine producing ability is increased, may be *Corynebacterium glutamicum* ATCC13032 strain (CA10-3101, KCCM12739P) into which hom(R407H) and ilvA(T381A,F383A) variations were introduced, or KCJI-38 strain (KCCM11248P, Korean Patent No. 10-1335789) which is an L-isoleucine-producing strain treated with N-methyl-N'-nitro-N-nitrosoguanidine (NTG), but is not limited thereto.

For example, the recombinant strain having the increased producing ability may have an increased L-isoleucine producing ability of about 1% or more, specifically, about 2% or more, about 5% or more, about 10% or more, about 15% or more, about 20% or more, about 25% or more, about 29% or more, about 30% or more, about 35% or more, about 39% or more, about 40% or more, about 41% or more, about 43% or more, about 45% or more, about 46% or more, about 50% or more, about 52% or more, about 55% or more, about 57% or more, about 58% or more, about 60% or more, or about 63% or more (the upper limit is not particularly limited, but may be, for example, about 200% or less, about 150% or less, about 100% or less, about 50% or less, about 40% or less, about 30% or less, about 20% or less, or about 15% or less), as compared to the L-isoleucine producing ability of the parent strain before being varied or an unmodified microorganism, but the increased amount is not limited thereto as long as the producing ability has an increased amount of a + value, as compared to the producing ability of the parent strain before being varied or an unmodified microorganism. In another example, the recombinant strain having the increased producing ability may have an increased L-isoleucine producing ability of about 1.01 times or more, about 1.02 times or more, about 1.05 times or more, about 1.10 times or more, about 1.15 times or more, about 1.20 times or more, about 1.25 times or more, about 1.29 times or more, about 1.30 times or more, about 1.35 times or more, about 1.40 times or more, about 1.41 times or more, about 1.43 times or more, about 1.45 times or more, about 1.46 times or more, about 1.50 times or more, about 1.52 times or more, about 1.55 times or more, about 1.57 times or more, about 1.60 times or more, or about 1.63 times or more (the upper limit is not particularly limited, but may be, for example, about 10 times or less, about 5 times or less, about 3 times or less, about 2 times or less), as compared to the L-isoleucine producing ability of the parent strain before being varied or an unmodified microorganism, but is not limited thereto.

As used herein, the term "unmodified microorganism" does not exclude strains including mutation that may occur naturally in microorganisms, and may be a wild-type strain or a natural strain itself or may be a strain before the trait is changed by genetic variation due to natural or artificial factors. For example, the unmodified microorganism may be a strain into which the acetohydroxy acid synthase variant described in the present specification is not introduced or has not yet been introduced. The term "unmodified microorganism" may be used interchangeably with "strain before being modified", "microorganism before being modified", "unvaried strain". "unmodified strain". "unvaried microorganism", or "reference microorganism".

In another example of the present disclosure, the microorganism of the present disclosure may be the genus *Corynebacterium* (*Corynebacterium stationis*), *Corynebacterium glutamicum, Corynebacterium crudilactis, Corynebacterium deserti, Corynebacterium efficiens, Corynebacterium callunae, Corynebacterium singulare, Corynebacterium halotolerans, Corynebacterium striatum, Corynebacterium ammoniagenes, Corynebacterium pollutisoli, Corynebacterium imitans, Corynebacterium testudinoris, or Corynebacterium flavescens*, specifically *Corynebacterium glutamicum*, but is not limited thereto.

As used herein, the term "enhancement" of polypeptide activity means that the activity of a polypeptide is increased, as compared to the endogenous activity. The enhancement may be used interchangeably with terms such as activation, up-regulation, overexpression, and increase, etc. Here, activation, enhancement, up-regulation, overexpression, and increase may include both exhibiting activity that was not originally possessed and exhibiting improved activity as compared to the endogenous activity or activity before modification. The "endogenous activity" means the activity of a specific polypeptide originally possessed by the parent strain before the trait is changed or an unmodified microorganism when the trait is changed by genetic variation due to natural or artificial factors. This may be used interchangeably with "activity before modification". The fact that the activity of a polypeptide is "enhanced", "up-regulated", "overexpressed", or "increased" as compared to the endogenous activity means that the activity of a polypeptide is improved as compared to the activity and/or concentration (expression level) of a specific polypeptide originally possessed by the parent strain before the trait is changed or an unmodified microorganism.

The enhancement may be achieved through the introduction of a foreign polypeptide or the enhancement of endogenous activity and/or concentration (expression level) of the polypeptide. The enhancement of the activity of a polypeptide may be confirmed by an increase in the degree of activity and the expression level of the corresponding polypeptide or in the amount of the product produced from the corresponding polypeptide.

For the enhancement of the activity of the polypeptide, various methods well known in the art may be applied, and the method is not limited as long as the activity of the polypeptide of interest may be enhanced as compared to that of the microorganism before being modified. Specifically, genetic engineering and/or protein engineering well known to those skilled in the art, which are routine methods of molecular biology, may be used, but the method is not limited thereto (e.g., Sitnicka et al. Functional Analysis of Genes. *Advances in Cell Biology.* 2010, Vol. 2. 1-16, Sambrook et al. *Molecular Cloning* 2012, etc.).

Specifically, the enhancement of the polypeptide of the present disclosure may be:

1) increase in the intracellular copy number of the polynucleotide encoding the polypeptide;
2) replacement of a gene expression regulatory region on a chromosome encoding the polypeptide with a sequence exhibiting strong activity;
3) modification of a start codon of a gene transcript encoding the polypeptide or a nucleotide sequence encoding a 5'-UTR region;
4) modification of the amino acid sequence of the polypeptide to enhance the activity of the polypeptide;
5) modification of the polynucleotide sequence encoding the polypeptide to enhance the activity of the polypeptide (e.g., modification of the polynucleotide sequence of the polypeptide gene to encode the polypeptide that has been modified to enhance the activity of the polypeptide);
6) introduction of a foreign polypeptide exhibiting the activity of the polypeptide or a foreign polynucleotide encoding the polypeptide;
7) codon optimization of the polynucleotide encoding the polypeptide;
8) analysis of the tertiary structure of the polypeptide to select and to modify or chemically modify the exposed site; or
9) a combination of two or more selected from 1) to 8), but is not particularly limited thereto.

More specifically:

1) The increase in the intracellular copy number of the polynucleotide encoding the polypeptide may be achieved by the introduction of, into a host cell, a vector which may replicate and function independently of the host and to which the polynucleotide encoding the corresponding polypeptide is operably linked.

Alternatively, the increase may be achieved by the introduction of one copy or two or more copies of the polynucleotide encoding the corresponding polypeptide into a chromosome of a host cell. The introduction into the chromosome may be performed by introducing a vector capable of inserting the polynucleotide into a chromosome of a host cell into the host cell, but is not limited thereto. The vector is as described above.

2) The replacement of a gene expression regulatory region (or expression control sequence) on a chromosome encoding the polypeptide with a sequence exhibiting strong activity may be, for example, deletion, insertion, non-conservative or conservative substitution, or occurrence of variation in a sequence due to a combination thereof or replacement with a sequence exhibiting stronger activity so that the activity of the expression regulatory region is further enhanced. The expression regulatory region may include, but is not particularly limited to, a promoter, an operator sequence, a sequence encoding a ribosome binding site, a sequence controlling the termination of transcription and translation, etc. For example, the replacement may be to replace the original promoter with a strong promoter, but is not limited thereto.

Examples of known strong promoters include cj1 to cj7 promoters (U.S. Pat. No. 7,662,943 B2), lac promoter, trp promoter, trc promoter, tac promoter, lambda phage PR promoter, PL promoter, tet promoter, gapA promoter, SPL7 promoter, SPL13(sm3) promoter (U.S. Pat. No. 10,584,338 B2), 02 promoter (U.S. Pat. No. 10,273,491 B2), tkt promoter, yccA promoter, etc., but is not limited thereto.

3) The modification of a start codon of a gene transcript encoding the polypeptide or a nucleotide sequence encoding a 5'-UTR region may be, for example, substitution with a base sequence encoding another start codon having a higher polypeptide expression rate as compared to an endogenous start codon, but is not limited thereto.

4) and 5) The modification of the amino acid sequence or the polynucleotide sequence may be deletion, insertion, non-conservative or conservative substitution of the amino acid sequence of the polypeptide or the polynucleotide sequence encoding the polypeptide or occurrence of variation in the sequence due to a combination thereof or replacement with an amino acid sequence or polynucleotide sequence modified to exhibit stronger activity or an amino acid sequence or polynucleotide sequence modified to be more active so that the activity of the polypeptide is enhanced, but is not limited thereto. The replacement may be specifically performed by inserting a polynucleotide into a chromosome by homologous recombination, but is not limited thereto. The vector used here may further include a selection marker for the confirmation of chromosome insertion. The selection marker is as described above.

6) The introduction of a foreign polynucleotide exhibiting the activity of the polypeptide may be introduction of a foreign polynucleotide encoding a polypeptide exhibiting activity the same as or similar to that of the polypeptide into a host cell. There is no limitation in its origin or sequence as long as it exhibits activity the same as or similar to that of the polypeptide. The introduction may be performed by appropriately selecting a known transformation method by those skilled in the art. As the introduced polynucleotide is expressed in a host cell, the polypeptide may be produced, and the activity thereof may be increased.

7) The codon optimization of the polynucleotide encoding the polypeptide may be codon optimization of an endogenous polynucleotide so as to increase transcription or translation in a host cell or codon optimization of a foreign polynucleotide so as to perform optimized transcription and translation in a host cell.

8) The analysis of the tertiary structure of the polypeptide to select and to modify or chemically modify the exposed site may be, for example, to determine a template protein candidate according to the degree of similarity of the sequence by comparing the sequence information of a polypeptide to be analyzed with a database storing the sequence information of known proteins, to confirm the structure based on this, and to modify or chemically modify the exposed site to be modified or chemically modified.

Such enhancement of the polypeptide activity may be an increase in the activity or concentration expression level of the corresponding polypeptide, based on the activity or concentration of the polypeptide expressed in a wild-type microbial strain or a microbial strain before being modified, or an increase in the amount of a product produced from the corresponding polypeptide, but is not limited thereto.

In the microorganism of the present disclosure, partial or entire modification of the polynucleotide may be induced by (a) homologous recombination using a vector for chromosome insertion in the microorganism or genome editing using engineered nuclease (e.g., CRISPR-Cas9) and/or (b) treatment with light such as ultraviolet rays and radiation, and/or chemicals, but is not limited thereto. A method of modifying a part or the entirety of the gene may include a method using a DNA recombination technology. For example, by introducing a nucleotide sequence or vector including a nucleotide sequence homologous to the gene of interest into the microorganism to cause homologous recombination, a part or the entirety of the gene may be deleted. The nucleotide sequence or vector to be introduced may include a dominant selection marker, but is not limited thereto.

In the microorganism of the present disclosure, the variant, polynucleotide. L-isoleucine, etc. are as described in other aspects.

Still another aspect of the present disclosure provides a method of producing L-isoleucine, the method including the step of culturing, in a medium, the strain of the genus *Corynebacterium* including the variant of the present disclosure or the polynucleotide of the present disclosure.

The method of producing L-isoleucine of the present disclosure may include the step of culturing, in a medium, the strain of the genus *Corynebacterium* including the variant of the present disclosure or the polynucleotide of the present disclosure or the vector of the present disclosure.

As used herein, the term "culturing" means growing the strain of the genus *Corynebacterium* of the present disclosure under appropriately controlled environmental conditions. The culturing process of the present disclosure may be performed according to suitable medium and culture conditions known in the art. Such a culture process may be easily adjusted and used by those skilled in the art according to the selected strain. Specifically, the culturing may be a batch type, continuous type, and/or fed-batch type, but is not limited thereto.

As used herein, the term "medium" means a mixed substance containing nutrients required to culture the strain of the genus *Corynebacterium* of the present disclosure as a main component, and the medium supplies nutrients, growth factors, etc., including water, which are indispensable for survival and development. Specifically, as the medium and other culture conditions used for culturing the strain of the genus *Corynebacterium* of the present disclosure, any one may be used without particular limitation as long as it is a medium used for common culture of microorganisms. The strain of the genus *Corynebacterium* of the present disclosure may be cultured in a common medium containing proper carbon sources, nitrogen sources, phosphorus sources, inorganic compounds, amino acids and/or vitamins, etc., while controlling the temperature, pH, etc. under aerobic conditions.

Specifically, the culture medium for the strain of the genus *Corynebacterium* may be found in the document "Manual of Methods for General Bacteriology" by the American Society for Bacteriology (Washington D.C., USA, 1981).

In the present disclosure, the carbon sources include carbohydrates such as glucose, saccharose, lactose, fructose, sucrose, maltose, etc.; sugar alcohols such as mannitol, sorbitol, etc., organic acids such as pyruvic acid, lactic acid, citric acid, etc.; amino acids such as glutamic acid, methionine, lysine, etc. Natural organic nutrients such as starch hydrolysate, molasses, blackstrap molasses, rice bran, cassava, sugarcane residue, and corn steep liquor may be used. Specifically, carbohydrates such as glucose and sterilized pretreated molasses (i.e., molasses converted to reducing sugar) may be used, and appropriate amounts of other carbon sources may be used in various manners without limitation. These carbon sources may be used singly or in combination of two or more thereof, but are not limited thereto.

As the nitrogen sources, inorganic nitrogen sources such as ammonia, ammonium sulfate, ammonium chloride, ammonium acetate, ammonium phosphate, ammonium carbonate, ammonium nitrate, etc.; and organic nitrogen sources such as amino acids such as glutamic acid, methionine, glutamine, etc., peptone, NZ-amine, meat extract, yeast extract, malt extract, corn steep liquor, casein hydrolysate, fish or decomposition products thereof, and skim soybean cake or decomposition products thereof may be used. These nitrogen sources may be used singly or in combination of two or more thereof, but are not limited thereto.

The phosphorus sources may include monopotassium phosphate, dipotassium phosphate, or sodium-containing salts corresponding thereto. As the inorganic compounds, sodium chloride, calcium chloride, iron chloride, magnesium sulfate, iron sulfate, manganese sulfate, calcium carbonate, etc. may be used. In addition, amino acids, vitamins and/or suitable precursors, etc. may be included. These components or precursors may be added to the medium batchwise or continuously, but is not limited thereto.

During the culturing of the strain of the genus *Corynebacterium* of the present disclosure, the pH of the medium may be adjusted by adding compounds such as ammonium hydroxide, potassium hydroxide, ammonia, phosphoric acid, sulfuric acid, etc. to the medium in a proper manner. During the culturing, foaming may be suppressed by using an antifoaming agent such as fatty acid polyglycol ester. Further, oxygen or oxygen-containing gas may be injected into the medium in order to maintain the aerobic state of the medium, or gas may not be injected or nitrogen, hydrogen, or carbon dioxide gas may be injected in order to maintain the anaerobic and microaerobic states, but is not limited thereto.

In the culturing of the present disclosure, the culture temperature may be maintained at 20° C. to 45° C., specifically, at 25° C. to 40° C., and the strain may be cultured for about 10 to 160 hours, but are not limited thereto.

The L-isoleucine produced through the culturing of the present disclosure may be secreted into the medium or may remain in the cells.

The method of producing L-isoleucine of the present disclosure may further include the steps of preparing the strain of the genus *Corynebacterium* of the present disclosure, preparing a medium for culturing the strain, or a combination thereof (in any order), for example, prior to the culturing step.

The method of producing L-isoleucine of the present disclosure may further include the step of recovering L-isoleucine from the medium according to the culturing (the medium subjected to the culturing) or from the strain of the genus *Corynebacterium*. The recovery step may be further included after the culturing step.

The recovery may be to collect L-isoleucine of interest by way of a suitable method known in the art according to the method of culturing the microorganism of the present disclosure, for example, a batch, continuous, or fed-batch culture method. For example, centrifugation, filtration, treatment with a crystallized protein precipitant (salting out), extraction, sonication, ultrafiltration, dialysis, various forms of chromatography such as molecular sieve chromatography (gel filtration), adsorption chromatography, ion-exchange chromatography, and affinity chromatography, etc., HPLC, or a combination thereof may be used. The L-isoleucine of interest may be recovered from the medium or microorganism by way of a suitable method known in the art.

The method of producing L-isoleucine of the present disclosure may further include a purification step. The purification may be performed by way of a suitable method known in the art. In an example, when the method of producing L-isoleucine of the present disclosure includes both the recovery step and the purification step, the recovery step and the purification step may be performed continuously or discontinuously regardless of the order, or may be performed simultaneously or by being combined into one step, but is not limited thereto.

In the method of the present disclosure, the variant, polynucleotide, vector, strain, etc. are as described in other aspects.

Still another aspect of the present disclosure provides a composition for producing L-isoleucine, the composition including the variant of the present disclosure, the polynucleotide encoding the variant, the vector including the polynucleotide, the strain of the genus *Corynebacterium* including the polynucleotide of the present disclosure; a culture medium thereof; or a combination of two or more thereof.

The composition of the present disclosure may further include arbitrary suitable excipients to be commonly used in compositions for producing amino acids. Such excipients may be, for example, a preservative, a wetting agent, a dispersing agent, a suspending agent, a buffering agent, a stabilizer, or an isotonic agent, etc., but are not limited thereto.

In the composition of the present disclosure, the variant, polynucleotide, vector, strain, medium, L-isoleucine, etc. are as described in other aspects.

Still another aspect of the present disclosure provides use of the variant of the present disclosure; the polynucleotide encoding the variant; or the strain of the genus *Corynebac-*

*terium* including the variant or the polynucleotide encoding the variant in the production of L-isoleucine.

MODE FOR CARRYING OUT THE INVENTION

Hereinafter, the present disclosure will be described in more detail by way of exemplary embodiments. However, the following exemplary embodiments are only preferred embodiments for illustrating the present disclosure, and thus are not intended to limit the scope of the present disclosure thereto. Meanwhile, technical matters not described in the present specification may be sufficiently understood and easily implemented by those skilled in the technical field of the present disclosure or similar technical fields.

Example 1: Preparation of L-Isoleucine-Producing Strain

Wild-type *Corynebacterium glutamicum* has an L-isoleucine producing ability, but does not produce L-isoleucine in excess. Therefore, in order to confirm a genetic trait that increases the L-isoleucine producing ability, a strain with an increased L-isoleucine producing ability as compared to the wild type was prepared.

First, in order to release the feedback inhibition of threonine, which is a precursor of isoleucine, in the L-isoleucine biosynthetic pathway of the wild-type *Corynebacterium glutamicum* ATCC13032, a gene hom encoding homoserine dehydrogenase was mutated to substitute histidine for arginine which is an amino acid at position 407 of homoserine dehydrogenase (Korean Patent No. 10-1996769).

In detail, in order to construct a vector for introducing the hom(R407H) variation onto the chromosome, PCR was performed using a primer pair of SEQ ID NO: 6 and SEQ ID NO: 7 or a primer pair of SEQ ID NO: 8 and SEQ ID NO: 9 using the chromosome of the wild-type *Corynebacterium glutamicum* ATCC13032 as a template, respectively. The primer sequences are as shown in Table 1 below.

TABLE 1

| SEQ ID NO. | Name | Sequence |
|---|---|---|
| 6 | Primer 1 | TCGAGCTCGGTACCCCGCTTTTGCACTCATCGAGC |
| 7 | Primer 2 | CACGATCAGATGTGCATCATCAT |
| 8 | Primer 3 | ATGATGATGCACATCTGATCGTG |
| 9 | Primer 4 | CTCTAGAGGATCCCCGAGCATCTTCCAAAACCTTG |

PfuUltra™ high-fidelity DNA polymerase (Stratagene) was used as a polymerase for PCR amplification, and PCR conditions were as follows: denaturation at 95° C. for 30 seconds; annealing at 55° C. for 30 seconds; and polymerization at 72° C. for 1 minute, and these conditions of denaturation, annealing, and polymerization were repeated for 28 cycles to obtain 1000 bp of a DNA fragment of the 5' upstream region and 1000 bp of a DNA fragment of the 3' downstream region, centering on the variation of the hom gene, respectively.

PCR was carried out using a primer pair of SEQ ID NO: 6 and SEQ ID NO: 9 using the amplified two PCR fragments as a template. After denaturation at 95° C. for 5 minutes, PCR was carried out for 28 cycles under conditions of denaturation at 95° C. for 30 seconds; annealing at 55° C. for 30 seconds; and polymerization at 72° C. for 2 minutes, and then polymerization was carried out at 72° C. for 5 minutes.

As a result, 2 kb of a DNA fragment (SEQ ID NO: 16) was amplified, the DNA fragment including the variation of hom gene encoding the homoserine dehydrogenase variant in which arginine at position 407 was substituted with histidine. The amplification product was purified using a PCR purification kit (QUIAGEN), and used as an insert DNA fragment for vector construction.

After treating the purified amplification product with a restriction enzyme smaI, a pDCM2 vector (Korean Patent Publication No. 10-2020-0136813) heat-treated at 65° C. for 20 minutes and the insert DNA fragment which is the amplification product were at a molar concentration (M) ratio of 1:2, and cloned using an infusion cloning kit (TaKaRa) according to the provided manual to construct a vector pDCM2-R407H for introducing the hom (R407H) variation onto the chromosome.

The constructed vector was transformed into *Corynebacterium glutamicum* ATCC13032 by electroporation, and a strain containing the hom(R407H) variation on the chromosome was obtained through a secondary crossing process, which was named *Corynebacterium glutamicum* ATCC13032 hom(R407H).

In order to increase feedback release and activity for L-isoleucine in the prepared ATCC13032 hom(R407H) strain, ilvA which is a gene encoding L-threonine dehydratase was mutated to substitute alanine for threonine which is an amino acid at position 381 and alanine for phenylalanine which is an amino acid at position 383 in L-threonine dehydratase.

In detail, in order to construct a vector for introducing the ilvA(T381A,F383A) variations onto the chromosome, PCR was carried out using a primer pair of SEQ ID NO: 10 and SEQ ID NO: 11 or a primer pair of SEQ ID NO: 12 and SEQ ID NO: 13 using the chromosome of wild-type *Corynebacterium glutamicum* ATCC13032 as a template, respectively. The primer sequences are as shown in Table 2 below.

TABLE 2

| SEQ ID NO. | Name | Sequence |
|---|---|---|
| 10 | Primer 5 | TCGAGCTCGGTACCCATGAGTGAAACATACGTGTC |
| 11 | Primer 6 | GCGCTTGAGGTACTCtgcCAGCGcGATGTCATCATCCGG |
| 12 | Primer 7 | CCGGATGATGACATCgCGCTGgcaGAGTACCTCAAGCGC |
| 13 | Primer 8 | CTCTAGAGGATCCCCCGTCACCGACACCTCCACA |

PfuUltra™ high-fidelity DNA polymerase (Stratagene) was used as a polymerase for PCR amplification, and PCR conditions were as follows: denaturation at 95° C. for 30 seconds; annealing at 55° C. for 30 seconds; and polymerization at 72° C. for 1 minute, and these conditions of denaturation, annealing, and polymerization were repeated for 28 cycles to obtain 1126 bp of a DNA fragment of the 5' upstream region and 286 bp of a DNA fragment of the 3' downstream region, centering on the variation of the ilvA gene, respectively.

PCR was carried out using a primer pair of SEQ ID NO: 10 and SEQ ID NO: 13 using the amplified two PCR fragments as a template. After denaturation at 95° C. for 5 minutes, PCR was carried out for 28 cycles under conditions of denaturation at 95° C. for 30 seconds; annealing at 55° C. for 30 seconds; and polymerization at 72° C. for 2 minutes, and then polymerization was carried out at 72° C. for 5 minutes.

As a result, 1.4 kb of a DNA fragment (SEQ ID NO: 17) was amplified, the DNA fragment including the variation of ilvA gene encoding the L-threonine dehydratase variant in which threonine at position 381 was substituted with alanine and phenylalanine at position 383 was substituted with alanine. The amplification product was purified using a PCR purification kit, and used as an insert DNA fragment for vector construction. After treating the purified amplification product with a restriction enzyme smaI, a pDCM2 vector heat-treated at 65° C. for 20 minutes and the insert DNA fragment which is the amplification product were at a molar concentration (M) ratio of 1:2, and cloned using an infusion cloning kit (TaKaRa) according to the provided manual to construct a vector pDCM2-ilvA(T381A,F383A) for introducing the ilvA(T381A,F383A) variations onto the chromosome.

The constructed vector was transformed into *Corynebacterium glutamicum* ATCC13032 hom(R407H) by electroporation, and a strain containing the ilvA(T381A,F383A) variations on the chromosome was obtained through a secondary crossing process, which was named *Corynebacterium glutamicum* CA10-3101.

The strain CA10-3101 was deposited to the Korea Culture Center of Microorganisms (KCCM), which is an international depositary authority under the Budapest Treaty, on May 27, 2020, and assigned Accession No. KCCM12739P.

Next, in order to confirm whether or not the introduction of the ilvA(T381A,F383A) variations into an L-isoleucine-producing strain actually increases L-isoleucine producing ability by increasing feedback release and activity for L-isoleucine, the following experiment was performed.

In detail, KCJI-38 strain (KCCM11248P, Korean Patent No. 10-1335789) which is an L-isoleucine-producing strain treated with N-methyl-N'-nitro-N-nitrosoguanidine (NTG) was introduced with the ilvA(T381A,F383A) variations by an electric pulse method to prepare KCCM11248P/pECCG117-ilvA(T381A,F383A) strain. A fermentation titration was then performed in the following manner.

The parent strain and the variant strain were inoculated into a 250 mL corner-baffled flask containing 25 mL of isoleucine production medium, and cultured at 32° C. for 60 hours with shaking at 200 rpm to produce L-isoleucine, respectively. The composition of the production medium is as follows.

<Production Medium>

10% glucose, 0.2% yeast extract, 1.6% ammonium sulfate, 0.1% potassium phosphate monobasic, 0.1% magnesium sulfate heptahydrate, 10 mg/L iron sulfate heptahydrate, 10 mg/L manganese sulfate monohydrate, 200 μg/L biotin, pH 7.2

After completion of the culture, L-isoleucine and L-threonine concentrations in the culture medium were measured for each tested strain using high-performance liquid chromatography (HPLC), and the results are shown in Table 3 below.

TABLE 3

| Name of strain | L-Isoleucine (g/L) | L-Threonine (g/L) |
|---|---|---|
| KCCM11248P (parent strain) | 1.5 | 0.5 |
| KCCM11248P/pECCG117-ilvA(T381A, F383A) | 4.0 | 0.0 |

As shown in Table 3, the KCCM11248P/pECCG117-ilvA (T381A,F383A) strain, into which the ilvA(T381A,F383A) variations were introduced, was confirmed to have the significantly increased L-isoleucine producing ability and to have a high L-threonine degradation rate, as compared to the parent strain KCCM11248P. Accordingly, it was confirmed that introduction of the ilvA(T381A,F383A) variations into the strain increases feedback release and activity for L-isoleucine.

Example 2: Preparation of ilvN Variant Library Vector

A variant library of the ilvN gene encoding the small subunit of acetohydroxy acid synthase (AHAS) was prepared. The library was prepared using an error-prone PCR kit (clontech Diversify® PCR Random Mutagenesis Kit), and a PCR reaction was carried out using the chromosome of wild-type *Corynebacterium glutamicum* ATCC13032 as a template and a primer pair of SEQ ID NO: 14 and SEQ ID NO: 15. The primer sequences are as shown in Table 4 below.

TABLE 4

| SEQ ID NO. | Name | Sequence |
|---|---|---|
| 14 | primer 9 | CGAGCTCGGTACCCATGGCTAATTCTGACG |
| 15 | primer 10 | TAGAGGATCCCCTTAGATCTTGGCCGGAGC |

In detail, under conditions where 0 to 3 variations per 1000 bl may occur, pre-heating was performed at 94° C. for 30 seconds, followed by 25 cycles of at 94° C. for 30 seconds and at 68° C. for 1 minute and 30 seconds. A PCR product thus obtained was subjected to 25 cycles of at 95° C. for 50 seconds, at 60° C. for 50 seconds, and at 68° C. for 12 minutes using a megaprimer (500 ng to 125 ng), and then treated with DpnI, and transformed into *E. coli* DH5a and spread on an LB solid medium containing kanamycin (25 mg/L). Twenty transformed colonies were selected and then plasmids were obtained, followed by analysis of the polynucleotide sequence. As a result, it was confirmed that variations were introduced at different sites at a frequency of 2 mutations/kb. About 20.000 transformed *E. coli* colonies were taken and plasmids were extracted therefrom, and designated as a pTOPO-ilvN-library.

Example 3: Preparation of ilvN Library-Introduced L-Isoleucine-Producing Strain The pTOPO-ilvN-library prepared in Example 2 was transformed into CA10-3101 (KCCM12739P), which is an L-isoleucine-producing strain prepared in Example 1, by electroporation, and then spread on a nutrient medium containing 25 mg/L of kanamycin to obtain 5,000 colonies of the strain, into which the variant gene was inserted. Each colony was named from CA10-3101/pTOPO-ilvNm5001 to CA10-3101/pTOPO-ilvNm10000.

In order to confirm colonies with the increased L-isoleucine producing ability among the obtained 5,000 colonies, each colony was subjected to fermentation titration in the following manner. In detail, the parent strain and the variant strain were inoculated into a 250 mL corner-baffled flask containing 25 mL of isoleucine production medium, respectively, and cultured at 32° C. for 60 hours with shaking at 200 rpm to produce L-isoleucine. The composition of the production medium is as follows.

<Production Medium>

10% glucose, 0.2% yeast extract, 1.6% ammonium sulfate, 0.1% potassium phosphate monobasic, 0.1% magnesium sulfate heptahydrate, 10 mg/L iron sulfate heptahydrate, 10 mg/L manganese sulfate monohydrate, 200 μg/L biotin, pH 7.2

After completion of the culture, L-isoleucine concentrations in the culture medium were measured for each tested strain using high-performance liquid chromatography (HPLC), and the results are shown in Table 5 below.

TABLE 5

| Name of strain | L-Isoleucine concentration (g/L) | Increase rate of L-isoleucine concentration (%) |
|---|---|---|
| CA10-3101(parent strain) | 2.01 | — |
| CA10-3101/pTOPO-ilvNm6289 | 2.91 | 45 |
| CA10-3101/pTOPO-ilvNm9011 | 3.16 | 57 |

As shown in Table 5, the three variant strains were confirmed to have the increased L-isoleucine producing ability, as compared to *Corynebacterium glutamicum* CA10-3101, which is the parent strain having ilvN WT. The two variant strains were subjected to sequencing, and as a result of comparing with the ilvN gene of the wild-type *Corynebacterium glutamicum* ATCC13032, the two variant strains were confirmed to include the following variations in the gene: CA10-3101/pTOPO-ilvNm6289 strain including a variation (A42V) in which valine was substituted for alanine, which is an amino acid at position 42 in the amino acid sequence of ilvN, and CA10-3101/pTOPO-ilvNm9011 strain including a variation (H47L) in which leucine was substituted for histidine, which is an amino acid at position 47 in the amino acid sequence of ilvN.

Based on the results, it was confirmed that the two variant strains (A42V,H47L) are able to produce L-isoleucine with high yield, as compared to the parent strain, and the increase rate of the L-isoleucine concentration of the strains, into which ilvN(A42V) and ilvN(H47L) were introduced, respectively, was about 45% and about 57%, respectively, as compared to the parent strain.

Example 4: Preparation of Variant ilvN-Introduced L-Isoleucine-Producing Strain The ilvN(A42V) and ilvN(H47L) variations confirmed in Example 3 were introduced into the *Corynebacterium glutamicum* CA10-3101 strain prepared in Example 1.

In detail, to construct a vector for introducing the variant ilvN gene (A42V,H47L) onto the chromosome, PCR was carried out using the chromosomes of CA10-3101/pTOPO-ilvNm6289 ilvN(A42V) and CA10-3101/pTOPO-ilvNm9011 ilvN(H47L) as a template and a primer pair of SEQ ID NO: 14 and SEQ ID NO: 15, respectively. PfuUltra™ high-fidelity DNA polymerase (Stratagene) was used as a polymerase for PCR amplification, and PCR conditions were as follows: denaturation at 95° C. for 30 seconds; annealing at 55° C. for 30 seconds; and polymerization at 72° C. for 1 minute, and these conditions of denaturation, annealing, and polymerization were repeated for 28 cycles to obtain two 545 bp DNA fragments, each including the variant ilvN gene (A42V,H47L). The amplification product was purified using a PCR purification kit (QUIAGEN), and used as an insert DNA fragment for vector construction. After treating the purified amplification product with a restriction enzyme smaI, a pDCM2 vector heat-treated at 65° C. for 20 minutes and the insert DNA fragment amplified through PCR were at a molar concentration (M) ratio of 1:2, and cloned using an infusion cloning kit (TaKaRa) according to the provided manual to construct pDCM2-ilvN(A42V) and pDCM2-ilvN(H47L) vectors for introducing the variant ilvN gene of *Corynebacterium glutamicum* onto the chromosome.

The constructed vector was transformed into *Corynebacterium glutamicum* CA10-3101 hom(R407H) by electroporation, and a strain having substitution of the variant ilvN on the chromosome was obtained through a secondary crossing process, and CA10-3101::ilvN(A42V) was named CA10-3129, and CA10-3101::ilvN(H47L) was named CA10-3130.

In order to examine the effect of increasing the L-isoleucine producing ability, the parent strain (CA10-3101) and the two variant strains (CA10-3129, CA10-3130) prepared in this Example were subjected to fermentation titration in the following manner, respectively.

The parent strain and the two variant strains were inoculated into a 250 mL corner-baffled flask containing 25 mL of isoleucine production medium, and cultured at 32° C. for 60 hours with shaking at 200 rpm to produce L-isoleucine. The composition of the production medium is as follows.

<Production Medium>

10% glucose, 0.2% yeast extract, 1.6% ammonium sulfate, 0.1% potassium phosphate monobasic, 0.1% magnesium sulfate heptahydrate, 10 mg/L iron sulfate heptahydrate, 10 mg/L manganese sulfate monohydrate, 200 μg/L biotin, pH 7.2

After completion of the culture, L-isoleucine concentrations in the culture medium were measured for each tested strain using high-performance liquid chromatography (HPLC), and the results are shown in Table 6 below.

TABLE 6

| Name of strain | L-Isoleucine concentration (g/L) | Increase rate of L-isoleucine concentration |
|---|---|---|
| CA10-3101 | 2.12 | — |
| CA10-3129 (A42V-introduced strain) | 3.10 | 46 |
| CA10-3130 (H47L-introduced strain) | 2.98 | 41 |

As shown in Table 6, it was confirmed that both the ilvN(A42V)-introduced CA10-3129 strain and the ilvN(H47L)-introduced CA10-3130 strain had the increased L-isoleucine concentration, as compared to the parent strain (CA10-3101), which is an L-isoleucine-producing strain having ilvN WT. The increase rate of the L-isoleucine concentration in the ilvN(A42V) or ilvN(H47L)-introduced strain was about 46% or about 41%, as compared to the parent strain.

Example 5: Construction of Combination Variant ilvN Plasmid

In order to introduce a combination of the two ilvN variants identified in Example 3 into the L-isoleucine strain, a vector for introducing the variant ilvN onto the chromosome was constructed.

In detail, PCR was carried out using pDCM2-ilvN(A42V) as a template and a primer pair of SEQ ID NO: 14 and SEQ ID NO: 20 or a primer pair of SEQ ID NO: 21 and SEQ ID NO: 15, and PCR was carried out using pDCM2-ilvN (H47L) as a template and a primer pair of SEQ ID NO: 14 and SEQ ID NO: 18 or a primer pair of SEQ ID NO: 19 and SEQ ID NO: 15. The primer sequences are as shown in Table 7 below.

TABLE 7

| SEQ ID NO. | Name | Sequence |
|---|---|---|
| 18 | Primer 11 | TTCGGTCTTAACAGACACGAGGGACACGAG |
| 19 | Primer 12 | GTGTCCCTCGTGTCTGTTAAGACCGAAACA |
| 20 | Primer 13 | CGGTTGATGCCgagTGTTTCGGTCTTTGCA |
| 21 | Primer 14 | AAGACCGAAACActcGGCATCAACCGCATC |

PfuUltra™ high-fidelity DNA polymerase (Stratagene) was used as a polymerase for PCR amplification, and PCR conditions were as follows: denaturation at 95° C. for 30 seconds; annealing at 55° C. for 30 seconds; and polymerization at 72° C. for 1 minute, and these conditions of denaturation, annealing, and polymerization were repeated for 28 cycles to obtain 166 bp and 405 bp DNA fragments. The amplification product was purified using a PCR purification kit (QUIAGEN), and used as an insert DNA fragment for vector construction. After treating the purified amplification product with a restriction enzyme smaI, a pDCM2 vector heat-treated at 65° C. for 20 minutes and the insert DNA fragment which is the amplification product were at a molar concentration (M) ratio of 1:2, and cloned using an infusion cloning kit (TaKaRa) according to the provided manual to construct a vector pDCM2-ilvN(A42V,H47L) for introducing the variant ilvN onto the chromosome.

Example 6: Preparation of Combination Variant ilvN-Introduced L-Isoleucine-Producing Strain The vector prepared in Example 5 was transformed into the *Corynebacterium glutamicum* CA10-3101 strain prepared in Example 1 by electroporation to obtain a strain in which the variant ilvN was substituted on the chromosome through a secondary crossing process. CA10-3101::ilvN (A42V,H47L) was named CA10-3132.

To examine the effect of increasing L-isoleucine productivity of the prepared strain, fermentation titration was performed in the following manner.

The parent strain and the variant strain were inoculated into a 250 mL corner-baffled flask containing 25 mL of isoleucine production medium, respectively, and cultured at 32° C. for 60 hours with shaking at 200 rpm to produce L-isoleucine. The composition of the production medium is as follows.

<Production Medium>

10% glucose, 0.2% yeast extract, 1.6% ammonium sulfate, 0.1% potassium phosphate monobasic, 0.1% magnesium sulfate heptahydrate, 10 mg/L iron sulfate heptahydrate, 10 mg/L manganese sulfate monohydrate, 200 μg/L biotin, pH 7.2

After completion of the culture, L-isoleucine concentrations in the culture medium were measured for each tested strain, and the results are shown in Table 8 below.

TABLE 8

| Name of strain | L-Isoleucine concentration (g/L) | Increase rate of L-isoleucine concentration (%) |
|---|---|---|
| CA10-3101 (parent strain) | 2.03 | — |
| CA10-3129(A42V) | 3.08 | 52 |
| CA10-3130(H47L) | 2.90 | 43 |
| CA10-3132(A42V, H47L) | 3.21 | 58 |

As shown in Table 8, the variant strains, each introduced with ilvN single variation (ilvN(A42V), ilvN(H47L)) or ilvN combination variation (ilvN(A42V, H47L)), showed the increased L-isoleucine concentration, as compared to the parent strain (CA10-3101), which is an L-isoleucine-producing strain having ilvN WT, and it was confirmed that the ilvN combination variation may increase the L-isoleucine producing ability of the strain, as compared to the ilvN single variation.

Example 7: Preparation of Variant ilvN-Substituted Strain from L-Isoleucine-Producing *Corynebacterium glutamicum* KCCM11248P Strain Two ilvN variations and combination variations, which were confirmed to be effective in increasing the L-isoleucine producing ability in Example 6, were introduced into the L-isoleucine-producing strain KCJI-38 (KCCM11248P, Korean Patent No. 10-1335789) treated with N-methyl-M-nitro-N-nitrosoguanidine (NTG) by an electric pulse method, and spread on a selection medium containing 25 mg/L kanamycin for transformation, and the variant ilvN-substituted strains and combination variant ilvN-substituted strains, each having substitution on the chromosome, were obtained through a secondary crossover process. The fermentation titration was then performed in the following manner.

The parent strain and the variant strain were inoculated into a 250 mL corner-baffled flask containing 25 mL of isoleucine production medium, respectively, and cultured at 32° C. for 60 hours with shaking at 200 rpm to produce L-isoleucine. The composition of the production medium is as follows.

<Production Medium>

10% glucose, 0.2% yeast extract, 1.6% ammonium sulfate, 0.1% potassium phosphate monobasic, 0.1% magnesium sulfate heptahydrate, 10 mg/L iron sulfate heptahydrate, 10 mg/L manganese sulfate monohydrate, 200 μg/L biotin, pH 7.2

After completion of the culture, L-isoleucine concentrations in the culture medium were measured for each tested strain using high-performance liquid chromatography (HPLC), and the results are shown in Table 9 below.

TABLE 9

| Name of strain | L-Isoleucine concentration (g/L) | Increase rate of L-isoleucine concentration (%) |
|---|---|---|
| KCCM11248P (parent strain) | 1.02 | — |
| KCCM11248PΔilvN::ilvN(A42V) | 1.43 | 40 |
| KCCM11248PΔilvN::ilvN(H47L) | 1.32 | 29 |
| KCCM11248PΔilvN:ilvN(A42V, H47L) | 1.66 | 63 |

As shown in Table 9, it was confirmed that the variant strains, each introduced with two ilvN variations or combination variation, showed the increased L-isoleucine concentration, as compared to the parent strain (KCCM11248P), which is an L-isoleucine-producing strain having ilvN WT, and it was confirmed that the increase rate of the L-isoleucine concentration in the ilvN(A42V)-, ilvN(H47L)-, or ilvN(A42V,H47L)-introduced strains were 40%, 29%, or 63%, respectively, as compared to the parent strain, indicating that the ilvN combination variation may increase the L-isoleucine producing ability of the strain, as compared to the ilvN single variation.

Based on the above description, it will be understood by those skilled in the art that the present disclosure may be implemented in a different specific form without changing the technical spirit or essential characteristics thereof. In this regard, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds are therefore intended to be embraced by the claims.

The invention claimed is:

1. A strain of the genus *Corynebacterium*, comprising (a) an acetohydroxy acid synthase (AHAS) variant in which an amino acid corresponding to position 42 and an amino acid corresponding to position 47 in an amino acid sequence of SEQ ID NO: 1 are each substituted with valine and leucine, wherein the variant has at least 90% identity to the amino acid sequence of SEQ ID NO: 1, or a polynucleotide encoding the variant; and (b) a homoserine dehydrogenase variant in which arginine at position 407 is substituted with histidine, or a gene encoding the variant; or an L-threonine dehydratase variant in which threonine at position 381 is substituted with alanine and phenylalanine at position 383 is substituted with alanine, or a gene encoding the variant, wherein the strain has an increased L-isoleucine producing ability, as compared to a strain of the genus *Corynebacterium* including a wild-type acetohydroxy acid synthase having an amino acid sequence of SEQ ID NO: 1 or a polynucleotide encoding the same.

2. The strain of claim 1, wherein the strain is *Corynebacterium glutamicum.*

3. A method of producing L-isoleucine, the method comprising culturing, in a medium, a strain of the genus *Corynebacterium,* recovering L-isoleucine from the medium or the strain of the genus *Corynebacterium,* wherein the strain comprises an acetohydroxy acid synthase (AHAS) variant in which an amino acid corresponding to position 42 and an amino acid corresponding to position 47 in an amino acid sequence of SEQ ID NO: 1 are each substituted with valine and leucine, wherein the variant has at least 90% identity to the amino acid sequence of SEQ ID NO: 1, or a polynucleotide encoding the variant.

4. A composition for producing L-isoleucine, the composition comprising the strain of the genus *Corynebacterium* of claim 1; a culture medium thereof; or a combination of two or more thereof.

5. The strain of claim 1, wherein the strain comprises a homoserine dehydrogenase variant in which arginine at position 407 is substituted with histidine, or a gene encoding the variant; and an L-threonine dehydratase variant in which threonine at position 381 is substituted with alanine and phenylalanine at position 383 is substituted with alanine, or a gene encoding the variant.

6. The strain of claim 1, wherein the acetohydroxy acid synthase (AHAS) variant comprises an amino acid sequence of SEQ ID NO: 5.

7. The strain of claim 1, the homoserine dehydrogenase variant is encoded by a nucleotide sequence of SEQ ID NO: 16.

8. The strain of claim 1, the L-threonine dehydratase variant is encoded by a nucleotide sequence of SEQ ID NO: 17.

9. The method of claim 3, wherein the acetohydroxy acid synthase (AHAS) variant comprises an amino acid sequence of SEQ ID NO: 5.

10. The method of claim 3, wherein the strain further comprises a homoserine dehydrogenase variant in which arginine at position 407 is substituted with histidine, or a gene encoding the variant; or an L-threonine dehydratase variant in which threonine at position 381 is substituted with alanine and phenylalanine at position 383 is substituted with alanine, or a gene encoding the variant.

11. The method of claim 10, wherein the strain further comprises a homoserine dehydrogenase variant in which arginine at position 407 is substituted with histidine, or a gene encoding the variant; and an L-threonine dehydratase variant in which threonine at position 381 is substituted with alanine and phenylalanine at position 383 is substituted with alanine, or a gene encoding the variant.

12. The method of claim 10, wherein the homoserine dehydrogenase variant is encoded by a nucleotide sequence of SEQ ID NO: 16.

13. The method of claim 10, wherein the L-threonine dehydratase variant is encoded by a nucleotide sequence of SEQ ID NO: 17.

* * * * *